United States Patent
Hees et al.

(10) Patent No.: US 10,494,486 B2
(45) Date of Patent: Dec. 3, 2019

(54) CONTINUOUS METHOD FOR REACTIONS WITH FINE-PARTICULATE ALKALI METAL DISPERSIONS

(71) Applicant: CHT Germany GmbH, Tübingen (DE)

(72) Inventors: Michael Hees, Meßstetten (DE); Ulrike Georgi, Tübingen (DE); Herbert Bachus, Hechingen (DE); Kai-Sven Müller, Achim (DE)

(73) Assignee: CHT Germany GmbH, Tübingen (DE)

( * ) Notice: Subject to any disclaimer, the term of this patent is extended or adjusted under 35 U.S.C. 154(b) by 114 days.

(21) Appl. No.: 15/771,768

(22) PCT Filed: Oct. 27, 2016

(86) PCT No.: PCT/EP2016/075956
§ 371 (c)(1),
(2) Date: Apr. 27, 2018

(87) PCT Pub. No.: WO2017/076744
PCT Pub. Date: May 11, 2017

(65) Prior Publication Data
US 2018/0346655 A1    Dec. 6, 2018

(30) Foreign Application Priority Data

Nov. 3, 2015 (DE) .................. 10 2015 221 529

(51) Int. Cl.
*B01J 8/00* (2006.01)
*C08G 77/00* (2006.01)
(Continued)

(52) U.S. Cl.
CPC ............ *C08G 77/80* (2013.01); *B01J 8/0015* (2013.01); *C07F 7/0827* (2013.01); *C08G 77/08* (2013.01);
(Continued)

(58) Field of Classification Search
None
See application file for complete search history.

(56) References Cited

U.S. PATENT DOCUMENTS

| 4,276,424 A | 6/1981 | Peterson, Jr. et al. |
| 4,324,901 A | 4/1982 | West et al. |
| 8,870,998 B2 | 10/2014 | Nolte et al. |

FOREIGN PATENT DOCUMENTS

| CN | 103508869 B | 4/2015 |
| DE | 1 281 684 B | 10/1968 |

(Continued)

OTHER PUBLICATIONS

Connolly et al. "The Wurtz Reaction of Chloromethyltrimethylsilane. A Classical Study" J. Org. Chem. 1964, 619-623. (Year: 1964).*
(Continued)

*Primary Examiner* — Robert S Loewe
(74) *Attorney, Agent, or Firm* — Clements Bernard Walker

(57) ABSTRACT

The invention relates to a method for carrying out organic reactions with fine-particulate alkali metal dispersions in a continuous operation, preferably on a rotary disc reactor. This method can be used primarily in the production of coupling products following Wurtz synthesis, and in the production of macrocycles using acyloin condensation.

9 Claims, 1 Drawing Sheet

(51) Int. Cl.
*C07F 7/08* (2006.01)
*C08G 77/08* (2006.01)

(52) U.S. Cl.
CPC .............. *B01J 2208/00752* (2013.01); *B01J 2219/00033* (2013.01)

(56) References Cited

FOREIGN PATENT DOCUMENTS

| | | |
|---|---|---|
| DE | 102012223260 A1 | 6/2014 |
| EP | 0 123 934 A1 | 3/1984 |
| EP | 0 382 651 A1 | 8/1990 |
| EP | 0 230 499 B1 | 7/1991 |
| EP | 0 632 086 B1 | 10/1999 |
| EP | 1 162 187 A2 | 12/2001 |
| EP | 1 206 460 B1 | 4/2003 |
| EP | 1 162 187 B1 | 12/2005 |
| EP | 1 152 823 B2 | 10/2006 |
| EP | 1 769 019 A1 | 4/2007 |
| EP | 1 862 477 B1 | 3/2013 |
| EP | 2 872 547 A1 | 5/2015 |
| GB | 896301 A | 5/1962 |
| JP | 2736916 B2 | 4/1998 |
| JP | 3087921 B2 | 7/2000 |
| WO | 02/18328 A1 | 3/2002 |

OTHER PUBLICATIONS

Bloomfield et al. "The Acyloin Condensation" Organic Reactions, 2004, 259-403. (Year: 2004).*
Jones et al. "Correlation of Structure and Molecular Weight Distributions during the Formation of Poly(methylphenylsilylene) by the Wurtz Reductive-Coupling Reaction" Organometallics, 1998, 17, 59-64. (Year: 1998).*
Jeoffrey Van Den Berg, "Successful Scale Up of Butyl-Lithium Using the SpinPro", Case, Chemistry, Efficient, Pharma, Reaction, Safe, Spinpro Reactor; Jul. 1, 2015.
Aktar et al., "Concentration of Apple Juice Using Spinning Disc Reactor Technology", J. Food Process Technology, vol. 2, Issue 2:108, 2011.
International Search Report for International Application No. PCT/EP2016/075956 dated Jan. 13, 2017.
Klaus Ruhlmann, "Die Umsetzung von Carbonsaureestern mit Natrium in Gegenwart von Trimethychlorsilan", Heruntergeladen von: East Carolina University. Urheberrechtlich geschutzt; Eingang: Jun. 18, 1970.
Stephen D. Pask et al.,"The spinning disk reactor: an example of a process intensification technology for polymers and particles", Polymer Chemistry, 2012, 3, 2698-2707, Jul. 3, 2012; www.rsc.org/polymers.
Aktar et al., "The use of spinning disc reactor for processing ice cream base—effect of ageing in making model ice cream", International Journal of Food Science and Technology 2009, 44, 1139-1145.
Boodhoo et al., "Classical Cationic Polymerization of Styrene in a Spinning Disc Reactor Using Silica-Supported BF3 Catalyst" Journal of Applied Polymer Science, vol. 101, 8-19 (2006); 2006 Wiley Periodicals, Inc.
Mohammadi et al.; "Synthesis of TiO2 nanoparticles in a spinning disc reactor", Chemical Engineering Journal 258 (2014) 171-184; journal homepage:www.elsevier.com/locate/cej.
Tinder et al.; "Whitepaper:Successful Scale Up of Butyl-Lithium using the SpinPro Reactor", www.flowid.nl/successful-scale-up-of-butyl-lithium-using-the-spinpro/; Apr. 7, 2016-May 3, 2017.
Boodhoo et al., "Continuous Photopolymerization in a Novel Thin Film Spinning Disc Reactor", Downloaded by Univ of Minnesota on Jul. 10, 2013/http://pubs.acs.org; Publication Date: Mar. 3, 2003; American Chemical Society.
Oxley et al., "Evaluation of Spinning Disk Reactor Technology for the Manufacture of Pharmaceuticals" Ind. Eng. Chem. Res. 2000, vol. 39, 2175-2182.
Boodhoo, "Spinning Disc Reactor for Green Processing and Synthesis"; 2013 John Wiley & Sons, Ltd. Published 2013 by John Wiley & Sons, Ltd.
Akhtar et al., "A novel continuous process for making mayonnaise and salad cream using the spinning disc reactor: Effect of heat treatment",http://dx.doi.org/10.1016/j.foodhyd.2014.06.007; Food Hydrocolloids 42 (2014) 223-228, journal homepage: www.elsevier.com/locate/foodhyd.
"Butyllithium" http://www.chemie.de/lexikon/Butyllithium.html, 1996.

* cited by examiner

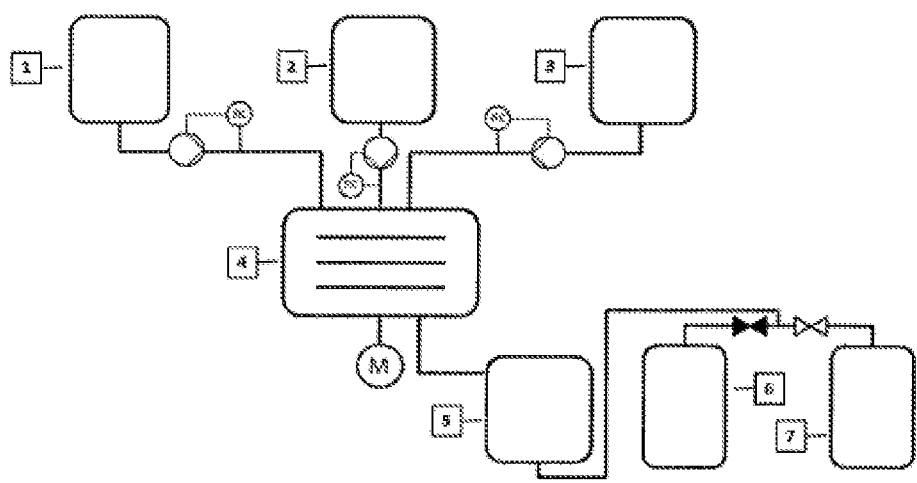

CONTINUOUS METHOD FOR REACTIONS WITH FINE-PARTICULATE ALKALI METAL DISPERSIONS

FIELD OF THE INVENTION

The present invention relates to a continuous process in which fine alkali metal dispersions are generated in organic solvents and employed for the coupling of organic esters and halides, and of organohalosilanes, in particular on a spinning disc reactor (SDR).

BACKGROUND OF THE INVENTION

Alkali metals, and among them especially sodium, have long been established in organic chemistry as reagents, for example for the production of alcoholates, for Darzens glycidic ester condensation, for the Birch reduction for conversion of aromatic to aliphatic compounds, or to acyloin condensation of esters to α-hydroxycarbonyl compounds (K. Rühlmann Synthesis (1971), 1971 (5), 236-253). In particular, the latter reaction is of importance in organic chemistry for the intramolecular cyclization of dicarboxylic acid esters to medium and large ring systems.

Another major field of application for elemental alkali metals is offered by the Wurtz coupling or Wurtz synthesis discovered in 1854 by French chemist Adolphe Wurtz, which initially served primarily for the synthesis of (cyclo) alkanes from haloalkanes. By means of the Wurtz synthesis, cycloalkanes having a ring size of from three to six carbon atoms are accessible. The Wurtz coupling is also the main route for the production of σ-π-conjugated silicon polymers through the polycondensation of halosilanes in aprotic organic solvents (R. D. Miller, J. Michl Chemical Reviews (1989), 89 (6), 1359-1410).

According to the current state of the art, the reactions above are performed in a semibatch process (described inter alia in the patents EP 0 123 934 B1, EP 0 632 086 B1, EP 0 382 651 A1, EP 1 769 019 A1, DE 10 2012 223 260 A1, EP 2 872 547 A1, EP 0 230 499 B1, JP 3087921 B2, JP 2736916 B2, CN 103 508 869 B, U.S. Pat. Nos. 4,324,901 A, 4,276,424 A). For this purpose, the suspension of an alkali metal (for example sodium) is charged in a reaction vessel. The substances to be coupled (haloalkanes, halosilanes or diesters/esters) are metered thereto under strictly controlled conditions, However, this method has a number of safety risks and procedural problems. On the one hand, the handling of the liquid alkali metals, but also of some of the reactants, such as the highly reactive chlorosilanes, on an industrial scale is very complex. Thus, moisture must be excluded completely at any rate. On the other hand, since the reaction is highly exothermic, the reproducibility of the product characteristics is influenced even by small variations within different batches. For example, even on a laboratory scale, a poor reproducibility of the results of a Wurtz coupling for the preparation of polysilanes is observed.

Since reactions with alkali metal dispersions are interfacial reactions, a dispersion as finely divided as possible and therefore a high particle surface are advantageous for quick and complete reactions. However, for a semibatch process, this is difficult to adjust exactly in production, resulting in disparities in the process. Also, an exact dosing of the reactants (for example, halogen compounds, esters) is essential for precise reaction control because different dosages can lead to deviations in the temperature course. For the above reasons, it is easy to understand that these factors also make the scaling-up of the semibatch process and the associated large-scale use of the reaction considerably more difficult.

For the reaction of alkali metals with alcohols above the melting point of the metals, a microreactor with a static mixer and heat exchanger with channel dimensions of around 500 μm was used in EP 1 162 187 B1.

The use of SDRs is prior art for the epoxidation of substituted cyclohexanones EP 1 206 460 B1, conversions of car boxy acids and esters WO 2002/018328 A1, the preparation of nanoparticles U.S. Pat. No. 8,870,998 B2, for the hydrogenation of nitrile rubber in solution EP 1 862 477 B1, for heterogeneously catalyzed reactions EP 1 152 823 B2, and for carrying out free-radical emulsion polymerizations U.S. Pat. No. 7,683,142 B2.

In addition, applications for the production of titanium dioxide particles are described in the scientific literature (S. Mohammadi; A. Harvey; K. V. K. Boodhoo Chemical Engineering Journal (2014), 258, 171-184), for the cationic polymerization of styrene using an immobilized catalyst (K. V. K. Boodhoo; W A E Dunk; M. Vicevic; R. J. Jachuck; V. Sage; D. J. Macquarrie, J. H. Clark Journal of Applied Polymer Science (2006), 101 (1), 8-19), for the photopolymerization of n-butyl acrylate (K. V. K, Boodhoo; W. A. E. Dunk; R. J. Jachuck ACS Symposium Series (2003), 847 (Photoinitiated Polymerization), 437-450), as well as for the production of mayonnaise (M. Akhtar; B. S. Murray, S. Dowu Food Hydrocolloids (2014), 42(S), 223-228), apple juice concentrate (M. Akhtar, P. Chan, N. Safriani, B. Murray, G. Clayton, Journal of Food Processing & Technology (2011), 2 (2), 1000108), and ice cream base emulsions (M. Akhtar; I. Blakemore; G. Clayton, S. Knapper, International Journal of Food Science and Technology (2009), 44 (6), 1139-1145). Furthermore, the company Flowid has realized a lithium halogen exchange at room temperature with a product flow of 100 kg/h of raw material or 20 kg/h of product for Biogen (http://www.flowid.nl/successful-scale-up-of-butyl-lithium-using-the-SpinPro/ 08.08.2015). In addition, many examples relating to recrystallization or particle synthesis are described in the literature. The benefits of SDR technology for these multiphase systems were discussed in detail in the literature and documented with examples (K. Boodhoo & A. Harvey, Process Intensification for Green Chemistry: Engineering Solutions for Sustainable Chemical Processing (2013), Chapter 3, John Wiley & Sons Ltd, pp 59-90), S. D. Pask, O. Nuyken, Z. Cai, Polymer Chemistry (2012), 3, 2698), P. Oxley, C. Brechteisbauer, F. Ricard, N. Lewis, C. Ramshaw, Industrial & Engineering Chemistry Research (2000), 39 (7), 2175-2182).

BRIEF SUMMARY OF THE INVENTION

Now, it is the object of the present invention to provide a continuous process for carrying out chemical reactions with liquid dispersions of finely divided alkali metals in inert solvents that is not limited by the described problems of the semibatch mode.

It has surprisingly been found that the above object is achieved in a first embodiment by the use of a device for carrying out continuous chemical reactions for the conversion of dispersions of finely divided alkali metals in inert solvents, in particular by the use of a spinning disc reactor for performing continuous chemical processes using liquid dispersions of finely divided alkali metals, alkali metal mixtures and/or alkali metal alloys in inert solvents.

Known systems of continuous production technology include so-called plug flow-reactors (PFRs), continuously stirred tank reactors (CSTR) and cascades thereof, as well as microreaction technology (MRI). For interfacial reactions at dispersed alkali metals, which are normally highly exothermic, highly efficient mixing is essential to ensure the highest possible mass flow of the reactants and products to or from the surface, and to quickly dissipate the heat produced thereby. This can be achieved, for example, with static mixers in flow tube or micro reactors. The latter further have an ideal distribution of dwelling times. Good mixing is also possible in CSTR's; they have the additional advantage that they are relatively easy to clean, whereby fouling or blocking in multiphase reactions (e.g., with two immiscible liquid components or solid reaction products) represents a minor problem.

A preferred system of continuous production technology, so far little employed technically, is a spinning disc reactor (SDR).

According to the invention, the essential problems of a semibatch procedure can be eliminated for the execution of reactions with finely divided dispersions of alkali metals by a continuous process: In a continuous reaction process, only small quantities of hazardous materials are brought together per unit time and thereby mixed efficiently in an ideal case. If a highly exothermic reaction is handled, the generated heat can be dissipated by a high surface-to-volume ratio, resulting in a homogeneous temperature profile in the reaction mixture. According to the invention, all this results in a significant improvement of the security aspect of such reactions, and in a significantly improved reproducibility of the product quality in the steady state of such a continuous process.

The present invention is employed, in particular, for the Wurtz coupling of halogen compounds, and for the acyloin condensation of esters. The liquid two-phase system, which is respectively present here, prior to the reaction or the concentrated salt dispersion formed in the Wurtz coupling does not result in fouling and blockages in continuously operating SDRs due to the high shear forces in this dynamic system.

BRIEF DESCRIPTION OF THE DRAWINGS

The present invention is illustrated and described herein with reference to the drawing, in which like reference numbers denote like method steps and/or system components, respectively, and in which:

FIG. 1 illustrates an exemplary flow diagram of the present invention.

DETAILED DESCRIPTION OF THE INVENTION

The reference symbol 1 represents a metering container with liquid alkali metal or alkali metal mixture/alloy; the reference symbol 2 represents a metering container of the reactant or reactant mixture; the reference symbol 3 represents a metering container of the solvent or solvent mixture; the reference symbol 4 represents a spinning disc reactor (SDR); the reference symbol 5 represents an optional dwelling time unit (for example, a stirred tank, a stirred tank cascade, a heat exchanger); the reference symbol 6 represents a collection container of the product mixture; the reference symbol 7 represents a collection container of the by-product mixture.

Because of the above examples, the spinning disc reactor could be developed as a suitable technology according to the invention for carrying out reactions with liquid alkali metal dispersions in inert organic solvents, especially the Wurtz coupling of halogen compounds, and the acyloin condensation, to form solid precipitates. This type of reactor has been developed for process intensification in order to optimize, in particular, heat transfer (heating, cooling, heat exchange) and mass transport processes (mixing, dispersing): This technology is based on one or more discs which are mounted horizontally on a rotating axis driven by an electric motor. A liquid applied to the surface of this disc is thrown to the edge of the plate or beyond by the action of the centrifugal acceleration. In the formed thin film, high shear forces are acting, and thus there are excellent heat and mass transfer rates. Thus, in highly exothermic reactions, the resulting heat can be dissipated quickly, and the mass transport maximized in diffusion-controlled processes. In addition, the high shear forces introduced in the liquid film flowing through lead to strong turbulence, which offers significant advantages, mainly in reactions in multiphase systems: Because of the high shear forces, the dispersed phase is very finely divided, and the interface between two immiscible phases maximized. This optimizes the mass transport to and from the interface. Further, the rotational motion is strong enough to propel solid deposits from the disc surface, creating a kind of self-cleaning mechanism, the fouling or blocking being reduced by the formation of precipitate.

The use described in this invention typically takes place in a liquid medium, which consists of an inert solvent or solvent mixture and the reactants dissolved therein (for example, haloalkanes, halosilanes, esters). In general, to achieve a high reaction rate, it is necessary that the alkali metal used or the alkali metal mixture or alloy used be in a molten state to disperse it in a finely divided state in the reaction medium. The alkali metal or alkali metal mixture or alloy, the reactants and solvents are each separately metered into the reactor. In the reaction of the alkali metal or alkali metal mixture or alloy with the reactants, an alkali metal salt insoluble in the reaction mixture is formed, and a coupling product, which may be soluble or insoluble in the liquid medium, depending on the type of reaction. It is thus a continuously performed multiphase reaction in which the reactive phases are present in a liquid form, and one or more reaction products are deposited as a solid precipitate.

All reaction steps are typically carried out under an inert gas atmosphere, in order to prevent side reactions due to oxygen or humidity, in particular the formation of hydrogen and hydrogen chloride.

In principle, all alkali metals, their mixtures and/or alloys are suitable for preparing the alkali metal dispersion. Preferred are the alkali metals or mixtures and/or alloys thereof whose melting point is in the range between −20 and 190° C. Especially preferred are lithium, sodium and potassium as well as their mixtures and alloys, since they are technically accessible and melt in a temperature range which is technically easy to handle.

As suitable inert solvents, all industrially common aprotic organic solvents can be employed in which the reactants (for example, halogen compounds of elements of Main Group IV or organic esters) are soluble, and which do not react with the alkali metal employed, or with the alkali metal mixture or alloy employed. Preferably used are hydrocarbons such as benzene, toluene, xylene and aliphatic hydrocarbons, and ethers such as dioxane, anisole and THF. The inert solvent may also be a mixture of the solvents mentioned, for example, of a hydrocarbon and an ether, i.e., for example, toluene and THF. Typically, the alkali metal salt formed in the reaction is not soluble in the solvent employed and can be separated off by filtration of the precipitate.

Different substances may be used as said reactants:

With the inventive method, all substrates common for Wurtz coupling, such as mono-, di-, tri- and polyfunctional alkyl and aryl halides, and mixtures thereof, and mono-, di-, tri- and polyfunctional haloorganosilanes and mixtures thereof can be reacted. Fluorine, chlorine, bromine and iodine can be used as said halogens in the halogen compounds, in particular, chlorine, bromine and iodine, preferably chlorine and bromine, are employed. In particular, the invention is suitable for the preparation of polysilanes and polycarbosilanes of halogenated organosilane building blocks that are no polysilanes. The halogenated organosilane components are defined by comprising less than 5 silicon atoms, preferably up to 3 silicon atoms, more preferably not more than 2 silicon atoms, and most preferably only one silicon atom.

For acyloin condensation, monoesters, diesters, triesters and polyesters are used. Preferably, mono- and diesters are used. In particular, the method described is suitable for the intramolecular cyclization of dicarboxylic acid esters to medium and large ring systems.

In the present invention, the amount of the solvent, the alkali metal and the reactants should be selected so that the reaction medium remains fluid even after formation of the solid precipitating alkali metal halides and the insoluble products, if any, so that fouling and blockage of the SDR remain minimized. Typically, from 5 to 99% by weight of solvent is employed, based on the total reaction mixture, preferably from 50 to 97% by weight, more preferably from 70 to 95% by weight of solvent fraction.

According to the invention, the ratio of the alkali metals employed or their mixtures and/or alloys to the reactants is selected so that a complete conversion is achieved. In the production of low molecular weight coupling products, a stoichiometric use, if possible, is preferred. For the preparation of polymeric coupling products, an excess of the alkali metal with respect to the halide, preferably an excess of up to 20% by weight, more preferably an excess of up to 10% by weight, even more preferably ex excess of up to 5% by weight, is typically required.

The process described in this invention can be carried out in a wide temperature range. The temperature range is limited by the fact that it is a multistage process with two fluids, more specifically the molten alkali metal or the molten alkali metal mixture or alloy, and the reaction medium of solvent and reactants. Thus, the melting temperature of the alkali metal or the alkali metal alloy/mixture results as the lower limit of the temperature range. The upper limit is determined by the boiling of the reaction mixture and the technical design of SDRs. Preferably, the reaction is carried out in a range between 50 and 200° C., more preferably between 100 and 115° C.

The rotational speed of the turntable of the SDR must be chosen so that an optimal dispersion of the liquid alkali metal or alkali metal mixture/alloy in the solvent is obtained.

A further advantage of the present invention is the high ratio of surface to volume of the reaction mixture, and the efficient mixing of this, whereby an efficient removal of the heat quantity generated in the exothermic reaction is possible. This results in a short dwelling time of the reaction mixture in the SDR and hence a short overall process time, with simultaneous reduction of the danger potential of the reaction. The resulting high space-time yield makes the process described economically highly interesting in comparison to established semibatch processes. Typically, the dwelling time of the reaction mixture in the SDR is <10 min, more preferably <5 min. During this time, most of the exothermic heat of the reaction is released and dissipated. In order to maximize the conversion of the reactive groups, especially in the preparation of a polymeric reaction product, a dwelling time unit may optionally be connected downstream. Here, all suitable units known in the art are suitable, in particular, a continuous stirred tank, a stirred tank cascade, a heat exchanger and temperature-controllable loop reactors.

When the reaction has reached the desired degree of conversion, the reaction product can be separated from the reaction mixture and optionally purified by any suitable method known in the art. For example, if the product is soluble in the reaction medium, the solid alkali metal salt precipitate is first separated off by filtration together with residual alkali metal, if any. Then, the product is obtained, for example, by fractional distillation or by distilling off the solvent. If the product is insoluble in the reaction medium, it can be removed by filtration together with the solid alkali metal salt precipitate and possibly residual alkali metal. Unreacted alkali metal is deactivated, if necessary, with protic solvents, and the alkali metal salts and extracted with water. These are examples.

EXAMPLES

For the reactions carried out, a commercially available SpinPro Reactor of the Company Flowid (Eindhoven, Netherlands, http://www.flowid.nl/spinpro-reactor/) with three turntables and an integrated heat exchanger was used. The distance between the turntables and the wall was 2 mm. The reactor volume was 230 ml. For all reactions, the reactor was evacuated 20 times for inerting and ventilated with 8 bar nitrogen. For the synthesis of polysilanes (Examples 1 and 2), a continuous stirred tank with a dwelling time of 20 min (flow rate 7.2 kg/h=>2.8 L; flow rate 10.8 kg/h=>4.1 L) was connected downstream of the SDR as a dwelling time unit.

Comparative Example

Semibatch Process for the Preparation of poly(methylphenylsilane)

Using standard Schlenk techniques, an apparatus comprising a 1000 mL four-necked flask with a dropping funnel, reflux condenser, KPG stirrer and temperature probe was evacuated and flooded with argon. In the four-necked flask, 215 g of xylene and 17.9 g of sodium were charged. The dropping funnel was filled with 67.3 g of dichloromethylphenylsilane, also under an inert gas atmosphere. With slow stirring, the flask was heated in an oil bath to about 102° C., so that the sodium was molten. Now, the agitation speed was set at exactly 300 rpm, and stirring was performed for about five minutes. After this time, a homogeneous, finely divided dispersion was formed (visual evaluation). To this suspension, the dichlorophenylmethylsilane was metered over a period of about 30 minutes. The start of the reaction could be observed by a rise in temperature, as well as an intense violet coloration of the reaction mixture. The metering rate was to be selected such that the dichlorophenylmethylsilane was added uniformly over the metering time while the reaction temperature is always kept within a temperature range of from 102 to 106° C.

After the end of the metering, the reaction mixture was stirred for a further 2 h at 102° C. After cooling to room temperature, the resulting suspension was filtered through a ceramic frit (G4) under a protective gas. The filtrate was concentrated by distilling off the solvent mixture under vacuum to obtain the soluble fraction of the poly(methylphenylsilane) formed. The polymer was characterized by $^1$H NMR, $^{13}$C NMR, $^{29}$Si NMR spectroscopy (each in $C_6D_6$) and gel permeation chromatography (in THF with light scattering detector).

Yield: 32%
Molar mass: 2000 g/mol
$^1$H NMR (δ [ppm], CDCl$_3$): 6.5-7.5 ppm, 0.5 ppm
$^{13}$C NMR (δ [ppm], CDCl$_3$): 134-138 ppm, 125-130 ppm, 21 ppm
$^{29}$Si-NMR (δ [ppm], CDCl$_3$): −41 ppm, −40 ppm, −39 ppm, +15 ppm Example 1—Continuous Preparation of poly(methylphenylsilane)

To start up the reaction, the SDR was adjusted to a rotational speed of 1000 or 2500 rpm, a heating oil temperature of 100 or 105° C., and at first a xylene flow rate of 6.5 kg/h. Once a constant temperature had become established in the reactor, the sodium metering was started. As soon as the discharge of a gray dispersion into the collecting vessel was observed, the metering of the dichloromethylphenylsilane was started. The mass ratio of dichloromethylphenylsilane to sodium was constant at 5/1 in all experiments. The start of the reaction was immediately recognizable by the temperature rise on the first and second plates of the reactor. Later, the deeply violet colored reaction mixture was discharged into the collection container. The metering rates and oil temperatures were varied as listed in the Table.

The product was filtered under nitrogen through a G4 ceramic frit, and the solvent was distilled off completely under vacuum. The polymer was characterized by $^1$H NMR, $^{13}$C NMR, $^{29}$Si NMR spectroscopy (each in $C_6D_6$) and gel permeation chromatography (in THF with light scattering detector).

metering was started at 10 g/min. The start of the reaction was immediately recognizable by the temperature rise in the reactor to 129° C. on the first plate. A little later, the deeply violet colored reaction mixture was discharged into the collection container. The product was filtered under nitrogen, and the solvent was distilled off. The polymer was characterized by $^1$H NMR, $^{13}$C NMR, $^{29}$Si NMR spectroscopy (each in $C_6D_6$) and gel permeation chromatography (in THF with light scattering detector).

GPC (eluent toluene, RI detector, calibration: polysiloxane standard): 300 g/mol, 900 g/mol
GPC (eluent THF, LS detector, sample-specific calibration): 1300 g/mol, D=1.6
$^1$H NMR (δ [ppm], CDCl$_3$): 6.5-7.5 ppm, 0.5 ppm.
$^{13}$C NMR (δ [ppm], CDCl$_3$): 134-138 ppm, 125-130 ppm, 21 ppm.
$^{29}$Si-NMR (δ [ppm], CDCl$_3$): −41 ppm, −40 ppm, −39 ppm.

Example 3—Cyclization of 1,6-dibromohexane to Cyclohexane

At a rotation speed of 2500 rpm, an oil temperature of 110° C. and a xylene flow rate of 6.5 kg/h, the sodium metering was started at 1.0 g/min. The temperature in the reactor leveled off at 122° C. As soon as the discharge of a gray dispersion from the reactor was observed, the metering of 1.6-dibromohexane was started at. 4 g/min. The start of the reaction was immediately recognizable by the temperature rise in the reactor to 127° C. on the first plate. A little later, the deeply violet colored reaction mixture was discharged into the collection container. The product was filtered off under nitrogen, the composition of the filtrate was analyzed by GC-MS, and a conversion of 98.5% was determined. The pure product was obtained by fractional distillation of the filtrate in 91% yield and analyzed by $^1$H and $^{13}$C NMR spectroscopy.

$^1$H NMR (δ [ppm], CDCl$_3$): 1.44.
$^{13}$C NMR (δ [ppm], CDCl$_3$): 26.9.

|  | Revolutions per minute [rpm] | $T_{heating\ oil}$ [°C.] | Total flow rate [kg/h] | Solids content [%] | $T_{1st/2nd/3rd\ plates}$ [° C.] | Molar mass [g/mol] | Yield of polysilane [%] |
| --- | --- | --- | --- | --- | --- | --- | --- |
| 1.1 | 2500 | 105 | 7.2 | 10 | 109/107/104 | 3100 | 46 |
| 1.2 | " | " | 10.8 | " | 112/108/105 | 2900 | 43 |
| 1.3 | 2500 | 105 | 10.8 | 20 | 119/114/109 | 1900 | 35 |
| 1.4 | " | " | 7.2 | " | 116/113/108 | 2200 | 38 |
| 1.5 | 1000 | 105 | 7.2 | 20 | 106/111/107 | 2400 | 41 |
| 1.6 | " | " | 10.8 | " | 107/118/109 | 2100 | 37 |
| 1.7 | 2500 | 100 | 10.8 | 20 | 110/106/101 | 2900 | 42 |
| 1.8 | " | " | 7.2 | " | 107/103/100 | 3200 | 47 |

$^1$H NMR (δ [ppm], CDCl$_3$): 6.5-7.5 ppm, 0.5 ppm.
$^{13}$C NMR (δ [ppm], CDCl$_3$): 134-138 ppm, 125-130 ppm, 21 ppm.
$^{29}$Si-NMR (δ [ppm], CDCl$_3$): −41 ppm, −40 ppm, −39 ppm, +15 ppm.

Example 2—Preparation of Cyclic oligo(methylphenylsilane)

At a rotation speed of 2500 rpm, a heating oil temperature of 125° C. and a xylene flow rate of 6.5 kg/h, the sodium metering was started at 2 g/min. The temperature in the reactor leveled off at 122° C. As soon as the discharge of a gray dispersion from the reactor was observed, the monomer

The invention claimed is:

1. A process for performing continuous chemical reactions for the conversion of dispersions of finely divided alkali metals in inert solvents comprising:

providing a first metering container containing a liquid alkali metal or alkali metal mixture or alloy, a second metering container containing a reactant or a reactant mixture, a third metering container containing a solvent or a solvent mixture, and a spinning disc reactor;

introduction of the solvent to the spinning a disc reactor;

metering the liquid alkali metal or alkali metal mixture or alloy into the spinning disc reactor; and metering the reactant or a reactant mixture into the spinning disc reactor and allowing a chemical process to occur.

2. The process according to claim 1, wherein the alkali metal or alkali metal mixture or alloy is lithium, sodium, potassium, mixtures thereof and/or alloys thereof.

3. The process according to claim 1, characterized in that the chemical process is a Wurtz synthesis.

4. The process according to claim 3, characterized in that mono-, di- or multifunctional halogen compounds of the elements of Main Group IV are employed as the reactants for said Wurtz synthesis.

5. The process according to claim 4 for preparing polysilanes from mono-, di- or multifunctional halosilanes and mixtures thereof.

6. The process according to claim 3 for preparing linear, branched and cyclic hydrocarbons from mono-, di- or multifunctional organic halogen compounds and mixtures thereof in the Wurtz synthesis.

7. The process according to claim 1, characterized in that the chemical process is an acyloin condensation.

8. The process according to claim 7, characterized in that organic mono-, di-, tri- or polyester compounds are employed as the reactants for said acyloin condensation.

9. The process according to claim 1, characterized in that said spinning disc reactor has a dwelling time unit connected downstream thereof.

\* \* \* \* \*

UNITED STATES PATENT AND TRADEMARK OFFICE
CERTIFICATE OF CORRECTION

PATENT NO. : 10,494,486 B2  
APPLICATION NO. : 15/771768  
DATED : December 3, 2019  
INVENTOR(S) : Hees et al.

Page 1 of 1

It is certified that error appears in the above-identified patent and that said Letters Patent is hereby corrected as shown below:

On the Title Page

Column 1, item (30) Foreign Application Priority Data  
Change "Nov. 3, 2015 . . . . . . . . . . . . 10 2015 221 529"  
To Nov. 3, 2015 . . . . . . . . . . . . 10 2015 221 529.6

Signed and Sealed this  
Twenty-first Day of January, 2020

Andrei Iancu  
*Director of the United States Patent and Trademark Office*